US00PP10586P

United States Patent [19]

Hofmann

[11] Patent Number: Plant 10,586

[45] Date of Patent: Sep. 1, 1998

[54] VARIETY OF GERANIUM NAMED 'MELODY RED'

[75] Inventor: Christa Hofmann, Grossdittmannsdorf, Germany

[73] Assignee: Elsner Pac Jungpflanzen, Germany

[21] Appl. No.: 746,399

[22] Filed: Nov. 8, 1996

[51] Int. Cl.[6] ..... A01H 5/00

[52] U.S. Cl. ..... Plt./87.12

[58] Field of Search ..... Plt./87.12

[56] References Cited

PUBLICATIONS

UPOV CD-ROM 97/03 Plant Breeders Rights to 'Peloda' in seven countries (NL, SE, IT, IL, DE, GB, NZ), 1993.

*Primary Examiner*—James R. Feyrer
*Assistant Examiner*—Melissa L. Kimball
*Attorney, Agent, or Firm*—Webb Ziesenheim Bruening Logsdon Orkin & Hanson, P.C.

[57] ABSTRACT

The new cultivar exhibits all of the positive qualities of "Melody." It is quick rooting, has very good cutting production and uniform size for improved finishing time. The new cultivar has elegant red flowers with big umbrels and flowers freely, early continuously.

1 Drawing Sheet

BACKGROUND OF THE INVENTION

The present invention comprises a new and distinct cultivar of *Pelargonium×hortorum* known by the varietal name 'Melody Red' ("PELODA" in Europe). The new cultivar was discovered at Elsner pac Jungpflanzen in Dresden, Germany in 1990. The new variety was discovered by crossbreeding several breeding lines, which are unnamed, but which are maintained proprietary for breeding purposes. The new variety bears cross number 90K-11-12, where 90 refers to the year, K to Kreuzung (cross), 11 to the color group and 12 to the 12th selected individual of the progeny of this cross. Group pollination was employed. The new variety was first asexually reproduced by cuttings at Elsner pac Jungpflanzen in Dresden following discovery, it has also been trial and field tested in Dresden, Germany and at Oglevee Ltd. in Connellsville, Pa. and has been found to retain its distinctive characteristics through successive propagations.

The plant history was taken on six week plants blossomed under the natural light in a greenhouse in 10 cm pots. The cultivar when grown in a glass greenhouse was potted on Feb. 13, 1996 and flowered on Mar. 25, 1996.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out by Oglevee, Ltd. in Connellsville, Pa. The plant history was taken on six week plants blossomed under natural light in a greenhouse and the color readings were taken indoors under 200–220 footcandles of cool white fluorescent light. Color references are primarily to the R.H.S. Colour Chart of The Royal Horticultural Society of London.

The Plant

Classification:

*Botanical.*—*Pelargonium×hortorum.*

*Commercial.*—Florists' zonal geranium.
*Form.*—Uniform, medium mound.
*Height.*—14.0–17.0 cm.
*Growth.*—Free and early flowering, basal branching.
*Strength.*—Stands upright without artificial support.
*Foliage.*—Stalked leaf attachment.

Leaves:
- *Size.*—7.0–9.0 cm.
- *Shape.*—Reniform.
- *Margin.*—Crenate.
- *Texture.*—Pubescent, smooth, reflective.
- *Color.*—Top: Green Group 137B. Bottom: Green Group 137D. Zone: Green Group 137A.
- *Ribs and veins.*—Venation: Palmate. Color: Yellow-Green Group 144A.

Petioles:
- *Color.*—Yellow-Green Group 144A.
- *Length.*—6.5–9.5 cm.

Stem:
- *Color.*—Yellow-Green Group 144A.
- *Internodes.*—1.0–1.5 cm in length.

The Bud (Umbel)

Shape: Upright hemispherical clusters.
Size (diameter): 4.0–4.3 cm, just cracking color.

Inflorescence

Blooming habit: Free and early flowering, semi-double, continuous.
Size (diameter): 4.5–7.0 cm, fully open bloom.
Borne: Umbel, floret on pedicel, pedicel on peduncle, flowers 7.0–9.5 cm above the foliage.

Florets:
- *Form.*—Flat to slightly cupped, slightly ruffled appearance due to petaloids.
- *Closed size.*—1.2 cm just cracking color.
- *Color.*—Top: Red Group 43A at outer edge, toward center is Red Group 40A, veins are Red Group 46A. Bottom: Red Group 40C with prominent dark veins of Red-Purple Group 57B.

Petals:
- *Quantity.*—6–7.
- *Size.*—2.0–3.0 cm.

Texture and appearance: Smooth, reflective.

Petaloids:
*Quantity.*—2–3.
*Shape.*—Irregular, twisted.
*Color.*—Top: Red Group 43A on outer edge, Red Group 40A toward center. Bottom: Red Group 40C.
Pedicel:
*Color.*—Red Group 53A with Yellow-Green Group 144C.
*Length.*—3.0 cm.
Peduncle:
*Color.*—Yellow-Green Group 144B.
*Length.*—18.5–21.0 cm.
Disease resistance: Not known.

Reproductive Organs

Stamens:
*Anthers.*—2.0 mm in length.
*Filaments.*—Color: White with a tint of Pink. Length: 5.0–6.0 mm.
*Pollen.*—Golden Brown.
Pistils:
*Number.*—1, 5–6 parted.
*Length.*—10.0 mm.
*Stigma.*—Color: Dark Red, Dark Purple.
*Style.*—Length: 3.0 mm.
*Ovaries.*—Pubescence: Superior, slightly pubescent. Length: 5.0 mm. Color: Green.
Fruit: None observed.

General Characteristics

1. Exhibits the positive flower characteristics of quantity, quality and duration of "Melody", U.S. Plant Pat. No. 8,006.

2. Quick rooting.

3. Very good cutting production.

4. Uniform size for improved finishing time.

5. Elegant flowers, big umbels and continuous flowering.

6. Early rich flowering.

I claim:

1. A new and distinct variety of geranium plant substantially shown and described.

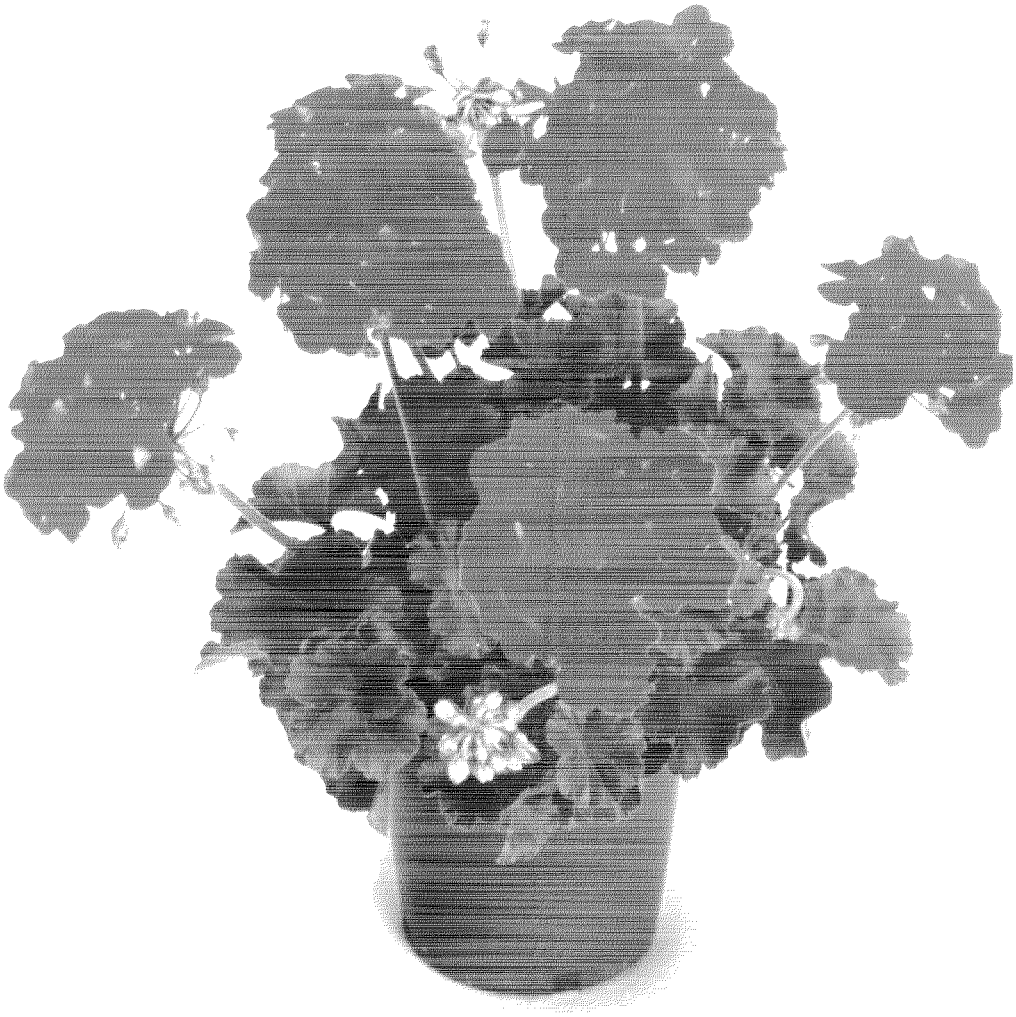

* * * * *